(12) United States Patent  
Takahashi et al.

(10) Patent No.: US 7,963,015 B2
(45) Date of Patent: Jun. 21, 2011

(54) METHOD OF SUPPRESSING EXTENSION OF FATIGUE CRACK, METHOD OF DETECTING FATIGUE CRACK AND PASTE USED FOR THE METHODS

(75) Inventors: Ichihiko Takahashi, Mitaka (JP); Chiori Takahashi, Mitaka (JP)

(73) Assignee: National Maritime Research Institute, Tokyo (JP)

( * ) Notice: Subject to any disclaimer, the term of this patent is extended or adjusted under 35 U.S.C. 154(b) by 1269 days.

(21) Appl. No.: 10/563,412

(22) PCT Filed: Jul. 1, 2004

(86) PCT No.: PCT/JP2004/009312
§ 371 (c)(1),
(2), (4) Date: Jan. 3, 2006

(87) PCT Pub. No.: WO2005/002782
PCT Pub. Date: Jan. 13, 2005

(65) Prior Publication Data
US 2006/0163332 A1    Jul. 27, 2006

(30) Foreign Application Priority Data
Jul. 7, 2003   (JP) ................................. 2003-193051

(51) Int. Cl.
*B22D 19/10*   (2006.01)
*B32B 5/16*    (2006.01)

(52) U.S. Cl. ..................................... 29/402.18; 428/404
(58) Field of Classification Search ............... 29/402.18, 29/402.01, 460; 228/248.1, 118; 403/265; 428/404
See application file for complete search history.

(56) References Cited

FOREIGN PATENT DOCUMENTS

| JP | 75005599 | * | 3/1975 |
| JP | 56-012552 | A | 2/1981 |
| JP | 62065485 | * | 3/1987 |
| JP | 5-57532 | A | 3/1993 |
| JP | 5-119032 | A | 5/1993 |
| JP | 8-029410 | A | 2/1996 |
| JP | 11-123617 | A | 5/1999 |

* cited by examiner

*Primary Examiner* — John C Hong
(74) *Attorney, Agent, or Firm* — Holtz, Holtz, Goodman & Chick, PC

(57) ABSTRACT

A method of detecting fatigue crack by which the fatigue crack can be easily detected by visual observation even in a relatively early stage, and a method of restraining propagation thereof. The detection method includes the steps of: (a) preparing a paste in which particles having hardness not less than that of a base material and an oil having viscosity are mixed with each other; (b) applying the paste to a desired portion of the base material; and (c) detecting fatigue crack based on a change in color generated by movement of base material powder to a surface of the paste, and the base material powder is produced when the particles grind the base material due to opening and closing of the fatigue crack in the base material.

6 Claims, 8 Drawing Sheets

- 2 FINE GRAIN PASTE
- SURFACE
- MICRO CRACK
- 1 BASE MATERIAL

TENSILE LOAD

TENSILE LOAD

COMPRESSIVE FORCE

METHOD OF SUPPRESSING EXTENSION OF FATIGUE CRACK, METHOD OF DETECTING FATIGUE CRACK AND PASTE USED FOR THE METHODS

This application is a U.S. National Phase Application under 35 USC 371 of International Application PCT/JP2004/009312 filed Jul. 1, 2004.

TECHNICAL FIELD

The present invention relates to a method of restraining growth of fatigue crack initiating in a surface of metal or the like, and a method of detecting the fatigue crack. Furthermore, the present invention relates to a paste to be used for those methods.

BACKGROUND ART

A fatigue phenomenon of metal is conventionally known that stresses are repeatedly applied to metal and micro crack (fatigue crack) initiates, even if the stresses are much lower than ultimate tensile strength. By further applying stresses repeatedly to the portion where the fatigue crack has initiated, the fatigue crack grows and leads to failure of metal. On the other hand, in a society at these days, metal is used everywhere. Accordingly, restraint of fatigue crack growth and early detection of fatigue crack are very important issues.

FIGS. 8A-8D are diagrams for explanation of initiation and growth of fatigue crack. As shown in FIG. 8A, micro crack initiates in a metal surface due to accumulation of fatigue damage by repeated stresses. Further, as shown in FIG. 8B, the crack opens by application of tensile load, and, as shown in FIG. 8C, the crack closes by removal of the tensile load. Furthermore, as shown in FIG. 8D, the crack opens by reapplication of tensile load. Thus, the crack propagates by repeating the opening and closing of the crack. Here, there is a problem that it is difficult to visually detect crack because the crack closes when no tensile load is applied as shown in FIGS. 8A and 8C.

As a related technology, Japanese Patent Application Publication JP-A-8-29410 (pp. 1-3 and FIG. 1) discloses a crack detection method of nondestructively detecting crack, which occurs randomly with respect to portions and orientations, at a high speed with high sensitivity. The method is usable in production lines for solid objects having black opaque appearance, rough surfaces and various shapes.

According to the crack detection method, the presence of crack can be easily detected by impregnating the crack with a volatile solvent such as acetone and benzene, leaving the sample with a dried surface in a sealed container at rest, and detecting the concentration of the volatile solvent that has vaporized and mixed in a carrier gas such as helium or nitrogen flowing along the surface of the sample.

However, in the crack detection method, even if the presence of crack has been detected, the portion where the crack of the sample is present cannot be detected. Further, since the sealed container is required, the detection is difficult with respect to a large-scaled sample such as a ship or aircraft. Therefore, in order to detect the portion where the crack of the sample is present, it is necessary to employ such technology as an ultrasonic flaw detection method, eddy-current flaw detection method, magnetic flaw detection method or staining flaw detection method as in the conventional detection.

Further, Japanese Patent Application Publication JP-A-56-12552 (pp. 1-2 and FIG. 1) discloses a crack detection method, by which even an inexperienced person can easily determine the presence or absence of flaw, without requiring a person having experience like the staining flaw detection method. After the application of the liquid and detection, it does not require application and removal of staining penetrating agent and developing agent like the staining flaw detection method, but requires only waiting for natural evaporation of a liquid.

According to the crack detection method, the presence of crack can be detected by impregnating a liquid such as water or ethyl alcohol in the crack, scanning the surface of the object with dried surfaces by using a temperature sensor or an alcohol sensor, and detecting the concentration of the vapor of the liquid remaining within the crack.

However, what is sensed by the sensor is the vapor in a range extremely near the sensor, and therefore, it is necessary to scan the entire object along the object surface in the crack detection method. Consequently, the detection takes much scanning time for a large-scaled object such as a ship or aircraft.

DISCLOSURE OF THE INVENTION

Accordingly, in view of the above-mentioned problems, a first object of the present invention is to provide a method of detecting fatigue crack by which fatigue crack can be easily detected by visual observation even in a relatively early stage. Further, a second object of the present invention is to provide a method of restraining fatigue crack growth. Furthermore, a third object of the present invention is to provide a paste to be used for those methods.

In order to solve the above-mentioned problems, a method of restraining fatigue crack growth according to one aspect of the present invention includes the steps of: (a) preparing a paste in which particles having hardness not less than that of a base material and an oil having viscosity are mixed with each other; and (b) applying the paste to a desired portion of the base material.

Further, a method of detecting fatigue crack according to one aspect of the present invention includes the steps of: (a) preparing a paste in which particles having hardness not less than that of the base material and an oil having viscosity are mixed with each other; (b) applying the paste to a desired portion of the base material; and (c) detecting fatigue crack based on a change in color generated by movement of base material powder to a surface of the paste, and the base material powder is produced when the particles grind the base material due to opening and closing of the fatigue crack in the base material.

Furthermore, a paste according to the present invention is a paste to be applied to a desired portion of a base material for restraining fatigue crack growth in the base material or detecting fatigue crack in the base material, and the paste includes: particles having diameters of 2 µm to 40 µm; and an oil having viscosity of 5,000 cP (centipoises) to 15,000 cP; wherein the particles and the oil are mixed with each other.

According to the present invention, a method of detecting fatigue crack by which fatigue crack can be easily detected by visual observation even in a relatively early stage can be provided. Further, a method of restraining fatigue crack growth and a paste to be used for those methods can be provided.

BEST MODE FOR CARRYING OUT THE INVENTION

Hereinafter, preferred embodiments of the present invention will be described in detail by referring to the drawings.

First, a method of restraining fatigue crack growth according to one embodiment of the present invention will be described. FIGS. 1A-1D are diagrams for explanation of the method of restraining fatigue crack growth according to one embodiment of the present invention.

First, a fine grain paste in a paste form is created by mixing fine particles of metal, ceramics or the like into an oil having appropriate viscosity. As shown in FIG. 1A, the fine grain paste 2 is applied to a surface of at least one portion where initiation and propagation of fatigue crack have been previously expected in a base material 1 of metal, reinforced plastic or the like.

Here, as the fine particles, a material having hardness equal to or larger than that of the base material is desirably used. For example, in the case where the base material is a metal having Vickers hardness of about 200 Hv, a material having Vickers hardness equal to or more than 200 Hv is used as the fine particles. The diameters of the fine particles are desirably made uniform in a range from about 2 μm to about 40 μm (an average is about 15 μm) by using sieves.

Further, as the oil into which the fine particles are mixed, an oil having viscosity of about 5,000 cP (centipoises) to about 15,000 cP is used. Here, 1000 cP=10P 20=1 Pa·s (pascal second). Especially, an oil having viscosity that varies little due to temperature change such as silicone grease is desirably used.

As shown in FIG. 1A, micro crack initiates in a metal surface due to accumulation of fatigue damage by repeated stresses. Further, as shown in FIG. 1B, the crack opens and grows by application of tensile load. The fine grain paste 2 enters the open crack because of the pumping action accompanied by opening and closing of the crack and the capillary phenomenon at the crack tip.

Here, as shown in FIG. 1C, even when the tensile load is removed, the fine grain paste 2 remains within the crack as a wedge and prevents the closing of the crack. Accordingly, as shown in FIG. 1D, when the tensile load is applied again, the displacement of the crack surface is restrained, and thereby, the growth rate of the crack due to opening and closing of the crack can be reduced and the fatigue life can be extended.

Next, an effect of crack growth restraint by the fine grain paste 2 will be described based on results of a fatigue test. FIG. 2 shows a shape of a test piece used as a base material to which a fine grain paste is applied in the fatigue test. As the base material, a test piece of aluminum-magnesium alloy JIS A5083P-O (manufactured by Nippon Light Metal Co., Ltd.) having a plate thickness of 5 mm has been used. As shown in FIG. 2, a hole having a diameter of 2 mm has been formed at the central part of the test piece and an artificial notch having a length of 10 mm and a width of 0.3 mm has been formed by electric discharge machining such that the artificial notch passes through the hole.

The fatigue test has been conducted by using an electro-hydraulic servo system fatigue testing machine having a dynamic capacity of 98 kN under complete pulsating load control with a load ratio R=0. The load waveform has been set to a sine wave, and a personal computer with a 32-bit CPU has been used for generating control signals and sampling load data in which the sampling frequency has been set to 200 Hz.

As the fine particles, iron magnetic particles for magnetic particle flaw detection (dry and gray, manufactured by Taiyo products co., Ltd.) and two types of alumina particles having different particle size distributions (manufactured by Powlex co., Ltd.) have been used. These fine particles have been mixed into oils to form pastes in a condition in which they do not drip, and applied to the notch portions and the expected crack propagation paths of the test pieces, respectively.

FIG. 3 shows relationships between nominal stress range $\Delta\sigma_n$ in portions having no notch and failure life $N_f$ in results of the fatigue test. Here, the symbol ● shows a test result in the case where nothing is applied, and the symbol ⊚ shows a test result in the case where only the oil is applied. The symbol ○ shows a test result in the case where a magnetic particle paste using magnetic particles (Fe) for magnetic particle flaw detection is applied.

Further, the symbol Δ shows a test result in the case where an alumina paste using alumina particles ($Al_2O_3$) having an average diameter of 47.3 μm is applied, and the symbol ∇ shows a test result in the case where an alumina paste using alumina particles ($Al_2O_3$) having an average diameter of 15.2 μm is applied.

As shown in FIG. 3, the failure life in the case where only the oil is applied is nearly equal to that in the case where nothing is applied. In contrast, the failure life in the case where the magnetic particle paste is applied is about 180,000 to 250,000 cycles longer than that in the case where nothing is applied. Therefore, it is conceivable that the wedge effect by the oil itself is negligible and the failure life extends because of the wedge effect by magnetic particles.

Further, the failure life in the case where the alumina paste using alumina particles having an average diameter of 47.3 μm is applied is nearly equal to that in the case where nothing is applied. The reason is conceivable as follows. In the case where the diameter is large, the suspensibility with oil is poor and alumina particles are not supplied to the crack tip.

In contrast, the failure life in the case where the alumina paste using alumina particles having an average diameter of 15.2 μm is applied is about 400,000 to 700,000 cycles longer than that in the case where nothing is applied. In this case, the most remarkable effect of crack growth restraint is obtained among the test results.

Next, a method of detecting fatigue crack according to one embodiment of the present invention will be described. FIGS. 4A and 4B are diagrams for explanation of the method of detecting fatigue crack according to the one embodiment of the present invention. The method of detecting fatigue crack according to the embodiment can be performed in conjunction with the above-mentioned method of restraining fatigue crack growth.

In the method of detecting fatigue crack according to the embodiment, a fine grain paste in a light-colored paste form is created by mixing light-colored fine particles like ceramics of alumina, zirconia or the like into an oil. Other conditions with respect to the fine particles and conditions with respect to the oil are the same as those in the above-mentioned method of restraining fatigue crack growth. In the embodiment, steel is used as the base material and white ceramics is used as the fine particles. In this case, the hardness of the fine particles is larger than that of the base material.

As described by referring to FIGS. 1A-1D, since the fine grain paste 2 remaining within the crack forms a wedge, the crack growth due to opening and closing of the crack can be restrained. In the opening and closing of the crack, as shown in FIG. 4A, when the tensile load is removed, the crack surface tends to close and a large compressive force is generated between the wedge of fine particles and the crack surface. Therefore, the fine particles having relatively larger hardness than that of the base material apply high pressure to the crack surface and partially grind the crack surface to pulverize the base material of the crack surface. Further, the fine particles are also pulverized by the compressive force into finer grains.

Furthermore, as shown in FIG. 4B, the base material powder is mixed with the oil of the fine grain paste 2 and the finer grains because of the pumping action accompanied by the opening and closing of the crack, and exudes to the surface of the fine grain paste 2. Since a metal powder generally takes on a black color, the fine grain paste 3 in which the base material powder is mixed takes on a black color. Here, since the fine grain paste 2 having no base material powder mixed therewith is white, a change in color appears due to the contrast between white and black, and the location, length, etc. of the crack can be easily and visually recognized.

Next, test results of the method of detecting fatigue crack according to the embodiment will be described. FIGS. 5A and 5B show a detection state and a propagation state of fatigue crack in high tension steel JIS SM490A having a shape as shown in FIG. 2. Here, FIG. 5A shows a state after tensile loading is repeated at 576,000 cycles, and FIG. 5B shows a state after tensile loading is repeated at 672,000 cycles. The vertical direction in FIGS. 5A and 5B is the loading direction.

As shown in FIG. 5A, since a black color representing a cracking portion develops on the white fine grain paste, the location, length, etc. of the crack can be easily and visually recognized. Further, the propagation state of the crack can be easily and visually recognized such that the black part in FIG. 5B extends longer than that in FIG. 5A.

FIGS. 6A and 6B show a shape of a test piece used for another test of the method of detecting fatigue crack. Here, FIG. 6A is a plan view of the test piece and FIG. 6B is a side view of the test piece. As shown in FIGS. 6A and 6B, the test piece is a welded joint test piece formed by welding two rib plates with one main plate and the material thereof is TMCP (thermo-mechanical control process) steel K32A.

FIGS. 7A and 7B show a detection state of crack in the welded joint test piece as shown in FIGS. 6A and 6B. Here, FIG. 7A shows a state before a fine grain paste is applied, and FIG. 7B shows a state after tensile loading is repeated at 1,200,000 cycles in the vertical direction in FIGS. 7A and 7B.

It is easy to imagine that fatigue crack will initiate in the welded portion as shown in FIG. 7A. Accordingly, the fine grain paste has been previously applied to the welded portion where initiation of fatigue crack is expected. Then, as shown in FIG. 7B, a black color develops on the white fine grain paste after tensile loading is repeated at 1,200,000 cycles, and thereby, the initiation and growth of crack can be easily and visually recognized.

According to the embodiment, fatigue crack can be easily recognized by visual test even in a relatively early stage, and the contribution to improvements in safety of various machines, structures, etc. can be made. Further, since the fine grain paste forms a wedge, the crack growth can be automatically restrained and the fatigue lives of various machines, structures, etc. can be extended. Furthermore, the method only requires to previously apply the fine grain paste to the portions, where initiation and propagation of fatigue crack is expected, for the detection and restraint of fatigue crack, it can be far easier and cheaper to perform compared with nondestructive detection methods such as an ultrasonic flaw detection method, penetration flaw detection method and magnetic flaw detection method.

INDUSTRIAL APPLICABILITY

The present invention can be utilized in a method of restraining fatigue crack growth in a surface of metal or the like, and a method of detecting the fatigue crack.

Figure 1A:
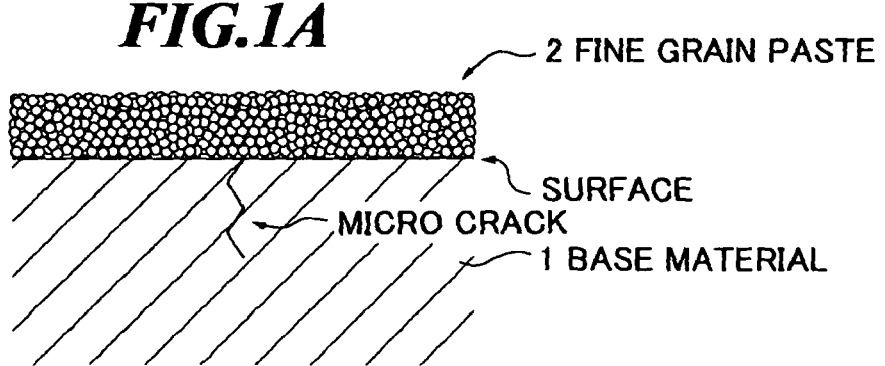
FIGS. 1A-1D are diagrams for explanation of a method of restraining fatigue crack growth according to one embodiment of the present invention.
Figure 1B:
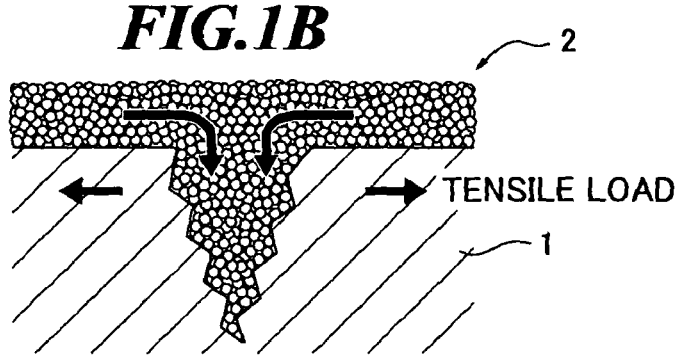
Figure 1C:
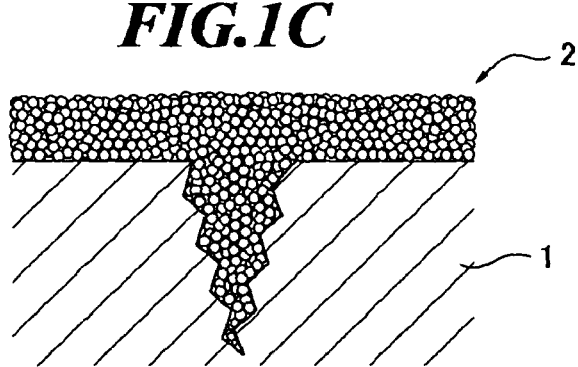
Figure 1D:
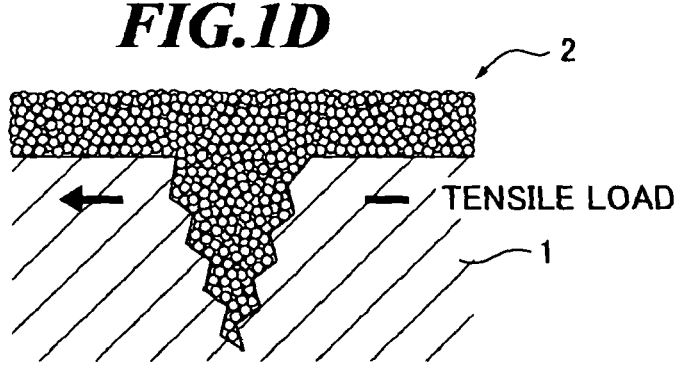
Figure 2:
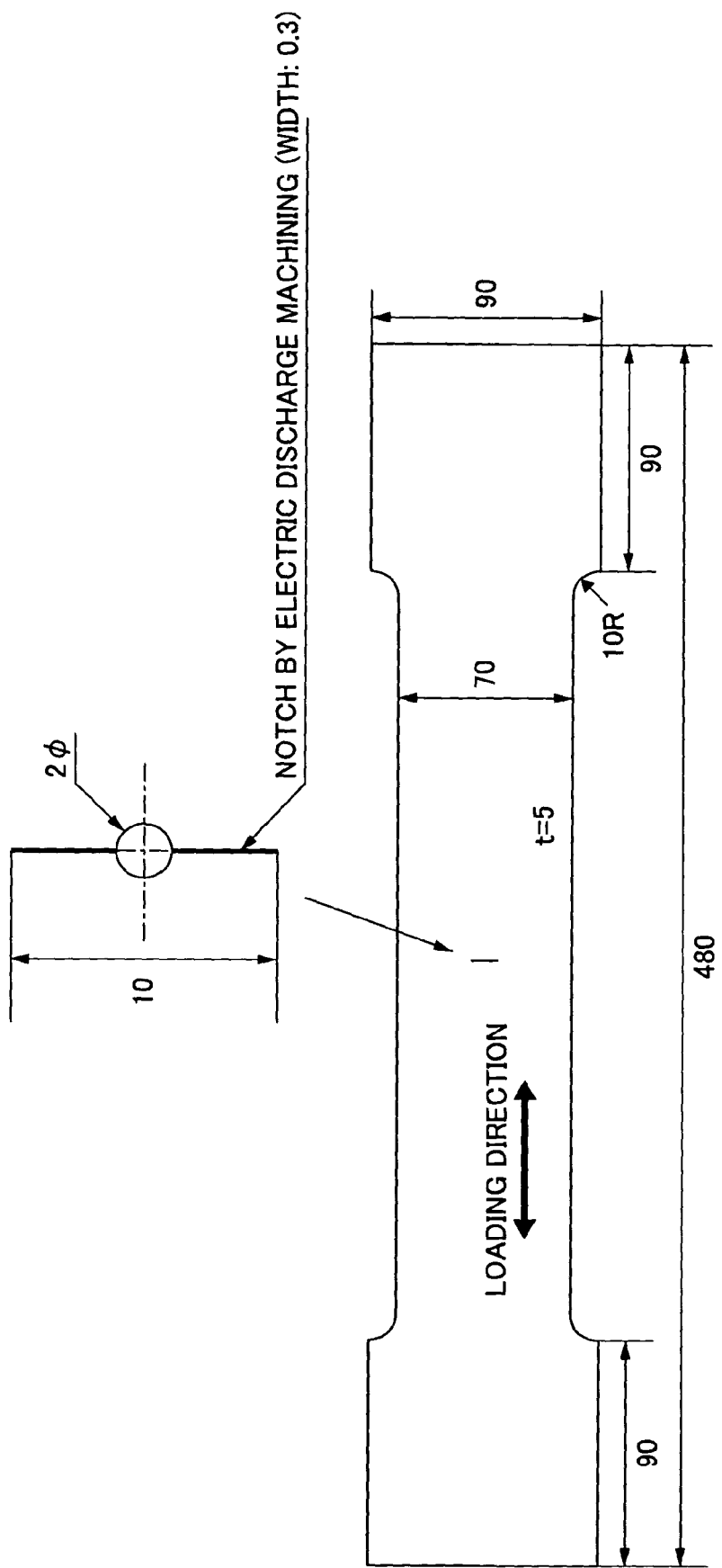
FIG. 2 is a diagram showing a shape of a test piece used as a base material to which a fine grain paste is applied in a fatigue test.
Figure 3:
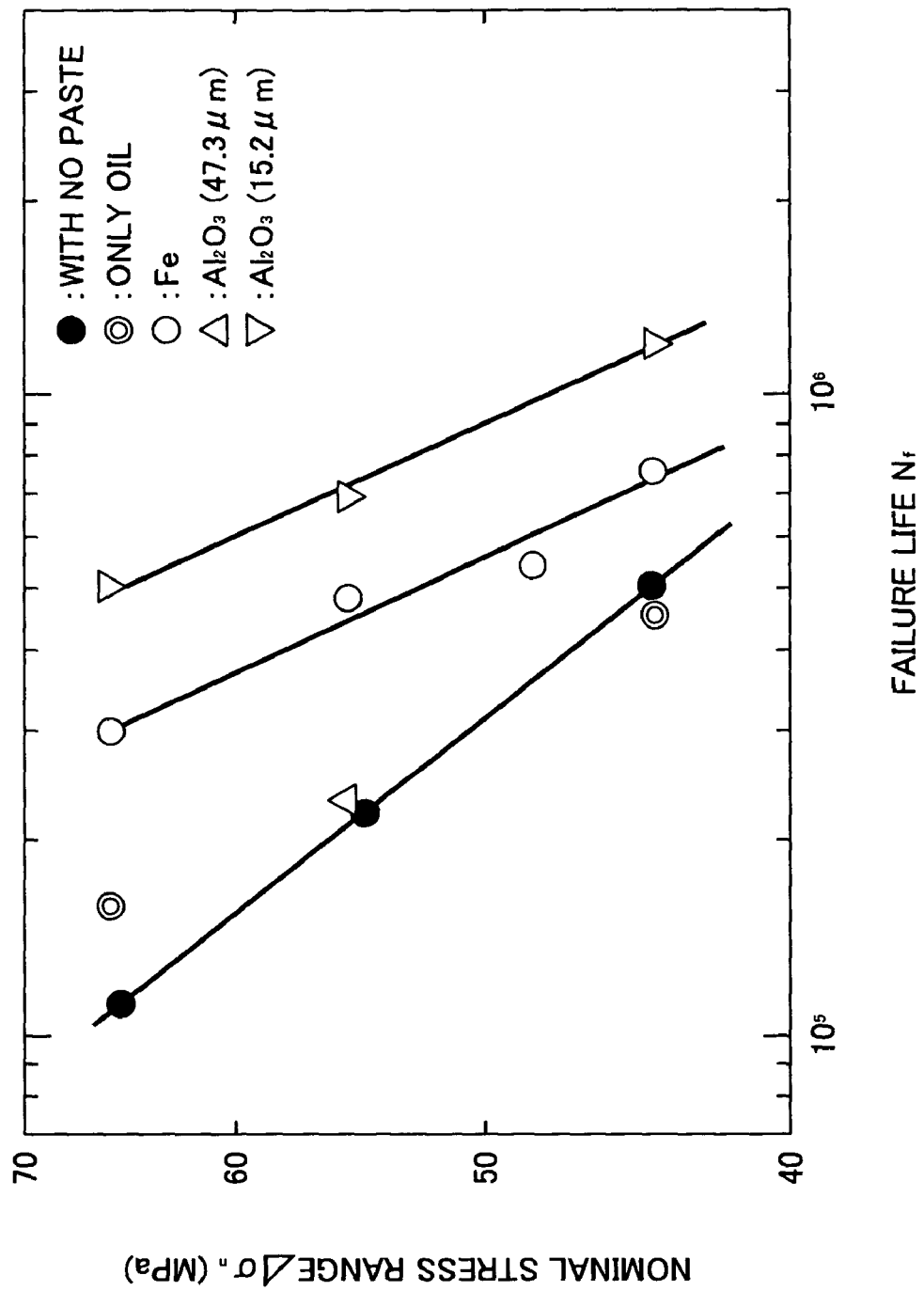
FIG. 3 is a diagram showing relationships between nominal stress range $\Delta\sigma_n$ and failure life $N_f$ in test results of the fatigue test.
Figure 4A:
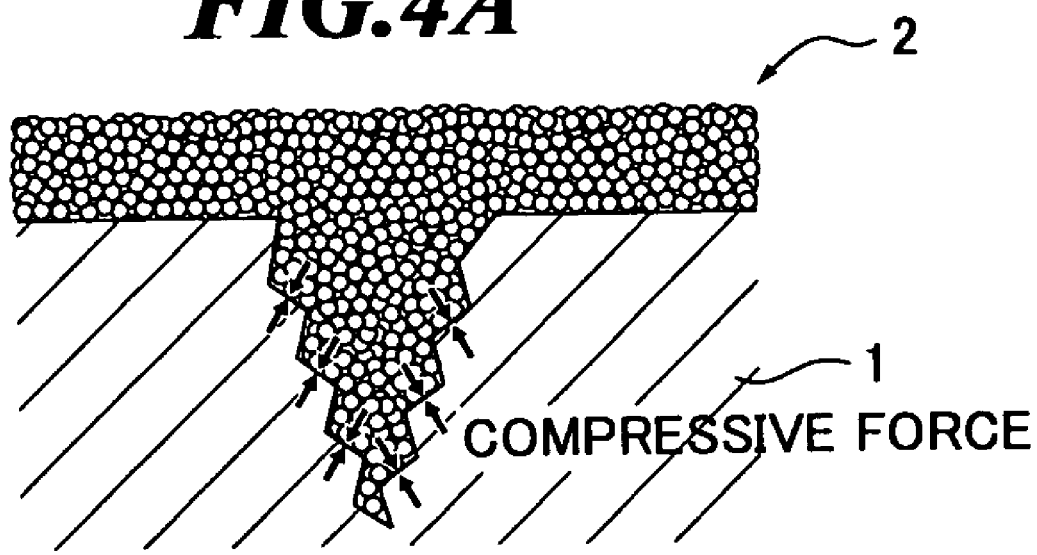
FIGS. 4A and 4B are diagrams for explanation of a method of detecting fatigue crack according to one embodiment of the present invention.
Figure 4B:
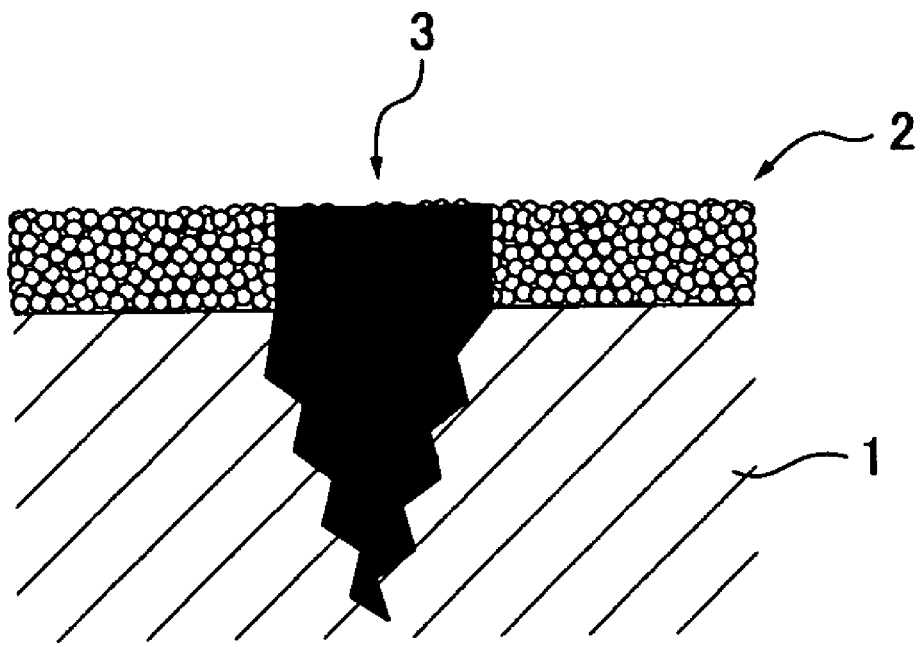
Figure 5A:
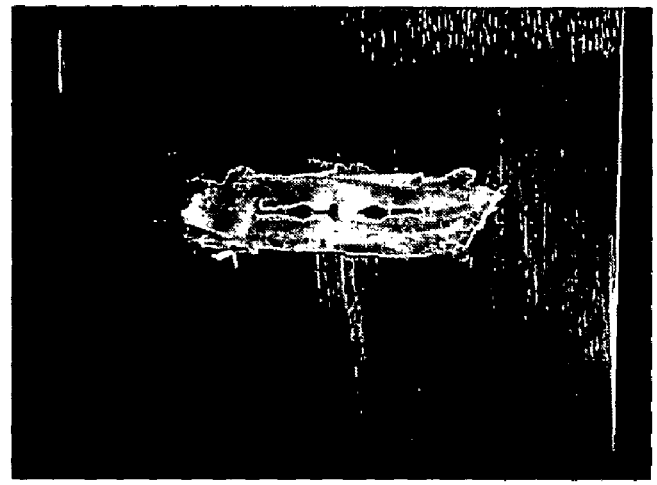
FIGS. 5A and 5B are diagrams showing a detection state and a propagation state of fatigue crack in a test piece of a high tension steel having a shape as shown in FIG. 2.
Figure 5B:
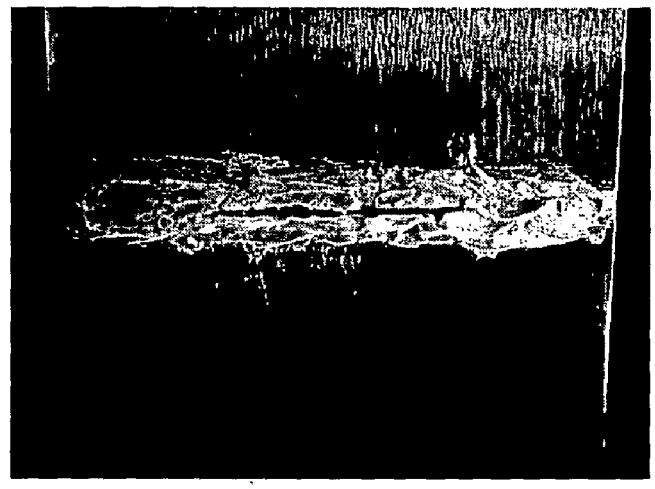
Figure 6A:
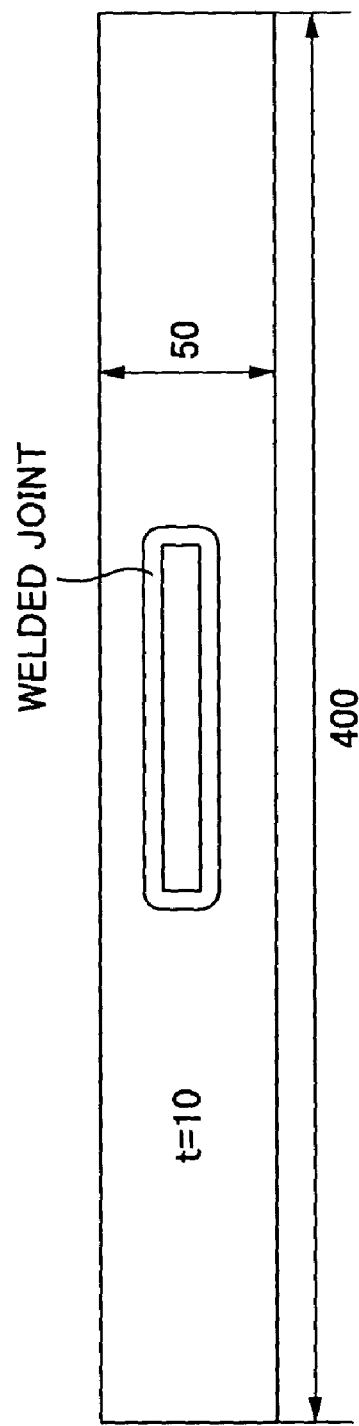
FIGS. 6A and 6B are diagrams showing a shape of a welded joint test piece used for another test of the method of detecting fatigue crack.
Figure 6B:
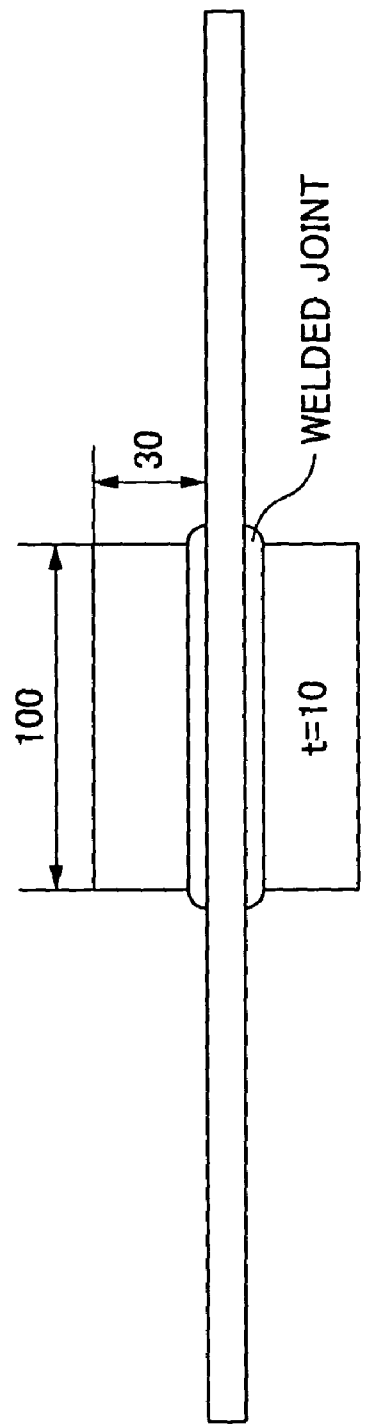
Figure 7A:
FIGS. 7A and 7B are diagrams showing a detection state of fatigue crack in a welded portion of the welded joint test piece as shown in FIGS. 6A and 6B.
Figure 7B:
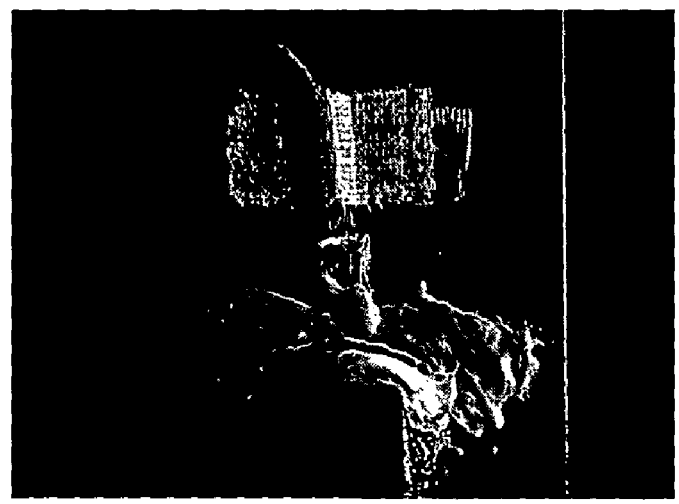
Figure 8A:
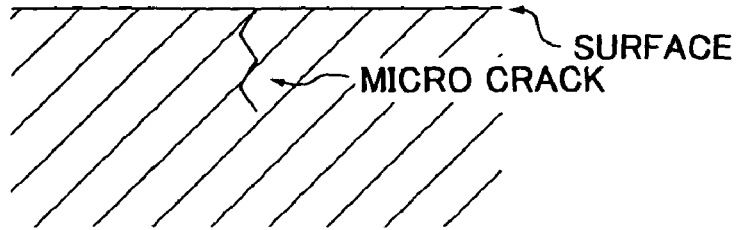
FIGS. 8A-8D are diagrams for explanation of initiation and propagation of fatigue crack.
Figure 8B:
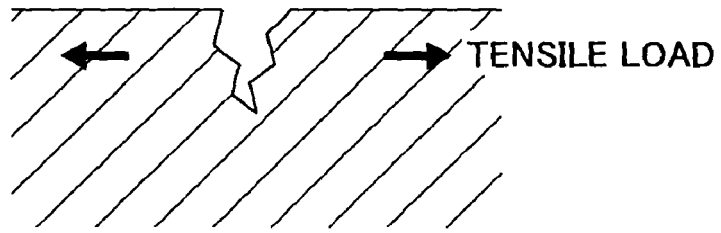
Figure 8C:
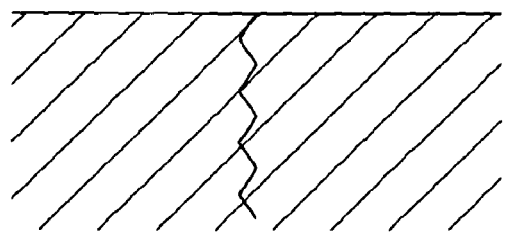
Figure 8D:
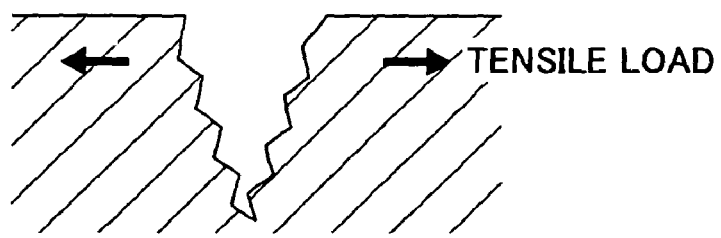

The invention claimed is:

1. A method of detecting fatigue crack in a base material, said method comprising:
   (a) preparing a paste in which particles having a hardness not less than a hardness of the base material and an oil having viscosity are mixed with each other;
   (b) applying said paste to a desired portion of said base material; and
   (c) detecting fatigue crack based on a change in color generated by movement of base material powder to a surface of said paste, said base material powder being produced when said base material at a surface of the fatigue crack is ground in contact with said particles due to opening and closing of the fatigue crack in said base material.

2. A method of detecting fatigue crack according to claim 1, wherein said particles comprise light-colored ceramics including white ceramics.

3. A method of detecting fatigue crack according to claim 1, wherein preparing the paste comprises:
   adjusting the oil to have a viscosity of 5,000 centipoises to 15,000 centipoises; and
   mixing said particles into the adjusted oil.

4. A method of detecting fatigue crack according to claim 2, wherein preparing the paste comprises:
   adjusting the oil to have a viscosity of 5,000 centipoises to 15,000 centipoises; and
   mixing said particles into the adjusted oil.

5. A paste to be applied to a desired portion of a base material for at least one of restraining fatigue crack growth in said base material and detecting fatigue crack in said base material, said paste comprising:
   particles having diameters of 2 µm to 40 µm, said particles comprising light-colored ceramics including white ceramics and having Vickers hardness of not less than 200 Hv; and
   an oil having a viscosity of 5,000 centipoises to 15,000 centipoises;
   wherein said particles and said oil are mixed with each other.

6. A paste according to claim 5, wherein said oil comprises silicone grease.

* * * * *